United States Patent
Cowe (10) Patent No.: US 8,088,111 B2
(45) Date of Patent: Jan. 3, 2012

(54) NEEDLE SHROUD ASSEMBLY

(75) Inventor: Toby Cowe, Oxford (GB)

(73) Assignee: Owen Mumford Limited, Oxford (GB)

( * ) Notice: Subject to any disclaimer, the term of this patent is extended or adjusted under 35 U.S.C. 154(b) by 0 days.

(21) Appl. No.: 12/065,512

(22) PCT Filed: Sep. 1, 2006

(86) PCT No.: PCT/GB2006/003248
§ 371 (c)(1), (2), (4) Date: Jun. 23, 2008

(87) PCT Pub. No.: WO2007/026164
PCT Pub. Date: Mar. 8, 2007

(65) Prior Publication Data
US 2008/0269691 A1    Oct. 30, 2008

(30) Foreign Application Priority Data
Sep. 1, 2005 (GB) .................................. 0517699.5

(51) Int. Cl.
*A61M 5/32* (2006.01)
(52) U.S. Cl. ......... 604/198; 604/192; 604/193; 604/533
(58) Field of Classification Search .................. 604/192, 604/193, 198, 533
See application file for complete search history.

(56) References Cited

U.S. PATENT DOCUMENTS

| | | | |
|---|---|---|---|
| 5,088,986 A | 2/1992 | Nusbaum | |
| 5,609,577 A | 3/1997 | Haber et al. | |
| 5,947,936 A | 9/1999 | Bonds | |
| 5,968,021 A * | 10/1999 | Ejlersen | 604/263 |
| 6,776,777 B2 * | 8/2004 | Barrelle | 604/198 |
| 6,852,096 B1 * | 2/2005 | Pouget et al. | 604/110 |
| 2003/0040725 A1 | 2/2003 | Hommann et al. | |
| 2004/0122379 A1 * | 6/2004 | Bosse et al. | 604/263 |

FOREIGN PATENT DOCUMENTS

| | | |
|---|---|---|
| WO | WO 92/20390 | 11/1992 |
| WO | WO 02/070053 | 9/2002 |
| WO | WO 02074369 | 9/2002 |

* cited by examiner

*Primary Examiner* — Kevin C Sirmons
*Assistant Examiner* — Brandy C Scott
(74) *Attorney, Agent, or Firm* — Young & Thompson

(57) ABSTRACT

A needle shroud assembly (10) comprises a barrel (16), a needle shroud (18) captively telescoped relative to the forward end of the barrel for movement between retracted and extended positions and is biased towards said extended position by a spring (25). A separate locking element (42) is mounted within the barrel moveable between a safe position (as seen in FIG. 5) in which it prevents or limits retraction movement of said needle shroud (18), and a live position in which it is clear of the rearward path of the needle shroud (18). The locking member is moved from its safe position to its live position by means of an externally operable actuating member (54), having a cam (52) which cooperates with a cam surface (46) on the locking element (42). The cam (52) is driven back to its original position by the rearward end of the shroud (18) as it moves to the fully retracted position.

19 Claims, 6 Drawing Sheets

NEEDLE SHROUD ASSEMBLY

This invention relates to needle shroud assemblies, and to parts therefor as well as to injection devices incorporating such needle shroud assemblies.

A medical syringe is often placed in a pen-like firing device or a holder of barrel form. The more sophisticated devices have a trigger which, when actuated, causes the dose to be administered automatically. The barrel-like holders make handling the syringe easier, but however the syringe is mounted, its needle has to project from the forward end, at least at the time of administering the dose. At other times, it is highly desirable for the syringe needle to be shrouded to prevent needle-stick injuries. It is also desirable to hide the needle in cases of patient needle phobia.

It is known to provide needle shroud assemblies in which an integral sprung latch is mounted on either the barrel or the shroud and is unlatched by pressing an externally accessible button so freeing the shroud for retraction movement. The use of an integral latch has problems associated with it because the design of the latch is inevitably a compromise between the requirement for the appropriate degree of flexural stiffness, the required robustness of the latch and the extent of the mutual abutment surfaces when the two items are latched together.

Accordingly, in one aspect, this invention provides a needle shroud assembly for a syringe holder, comprising:

a barrel, a needle shroud captively telescoped relative to the forward end of the barrel, for movement between extended and retracted positions, shroud bias means urging said shroud towards said extended position, a separate locking element movably mounted on one of said needle shroud and said barrel and movable between a safe position in which it prevents or limits retraction movement of said needle shroud, and a live position in which retraction movement is not blocked thereby, and an externally operable actuating member movable to a release position to drive said locking element to its live position.

In this arrangement, the provision of a separate locking element means that some if not of the all above design constraints on the latch are freed, thereby allowing provision of a robust locking assembly.

Preferably, the locking element is a saddle-shaped element of generally arcuate or part-cylindrical form. This allows an extended contact surface between the locking element and the shroud when abutting. The locking element is preferably pivotable or rockable between said safe and live positions.

The locking element preferably includes separate bias means urging it towards said safe position. Although either arrangement is possible, it is preferred for the locking element to be movably mounted on said barrel, defining an extended arcuate abutment surface for cooperating with an associated region on said needle shroud when in the safe position.

The drive arrangement between the actuating member and the locking element taken many different forms, but in a preferred arrangement may comprise at least one camming surface which cooperates with a corresponding cam element associated with, or forming part of, said actuating member, whereby longitudinal movement of said actuating member in the appropriate sense towards a release position drives the locking element to its live position. The cam element/camming surface arrangement provides a reliable displacement mechanism and furthermore, allows the actuating member to be designed so that it is readily operated by the frail or those of impaired dexterity. Other drives in which a longitudinal movement of said actuating member moves the locking element from its safe to its live position may be used.

Preferably, the camming surface includes a detent region whereby on moving said actuating member to said release position it is retained there by cooperation of the cam follower and the detent region. This provides a positive click for user confidence and also prevents inadvertent return of the locking member to its safe position. In a particularly preferred embodiment, the needle shroud is adapted so that, as it moves towards its retracted position, a surface thereon cooperates with said actuating member to move it from the release position back to its original position.

Preferably, said shroud bias means comprises a compression spring acting between a distal region of the shroud and a grip ring which in use engages a needle tip device of the syringe.

In one embodiment, where the needle tip device is screwed onto the syringe to attach it, the grip ring is dimensioned in use non-rotatably to engage, or to be engageable with, a flange or collar of the needle assembly, whereby in use, said needle tip assembly may be unscrewed by rotating said needle shroud assembly relative to said syringe.

In one arrangement, said grip ring is generally of ovoid or of oblate circular internal cross-section whereby in use the grip ring may grip the needle tip assembly between its narrower dimension during unscrewing and then may be released from the grip ring by applying compression generally along the axis of greatest diameter of said section. The term 'diameter' is used in the context of non-circular shapes to mean that dimension which would equate to the diameter if the article was circular. It will of course be appreciated that instead of the grip ring being configured to release the needle tip assembly when squeezed, the grip ring may be circular or non-circular and arranged to fit with clearance over the needle tip assembly and to be resiliently compressible so that the needle tip assembly may be temporarily gripped by squeezing the grip ring.

Preferably, the grip ring includes an operating button, said button being located in a longitudinal slot on said needle shroud so as to be externally accessible. In the first instance described above, where the ring is of ovoid or oblate circular form, the button will usually be generally aligned with the axis of greatest diameter. Preferably, the grip ring has a castellated or splined inner cylindrical for cooperating with a corresponding shaped surface on said needle tip device in axially engageable manner.

In another aspect, this invention provides a needle shroud assembly for cooperating in use with a syringe having a needle tip device screwed thereon, comprising a needle shroud for shrouding said needle and slidably mounted with respect thereto a grip ring adapted in use non-rotatably to engage, or be engageable with, said needle tip device to allow unscrewing thereof, said grip ring being selected with regard to the needle tip assembly such that in a first configuration said grip ring grips said needle tip assembly non-rotatably and in a second configuration said grip ring fits with clearance around said needle tip assembly to allow release thereof, wherein one of said first and second configurations is a resiliently compressed state and the other is a relaxed state. In one arrangement said grip ring is of ovoid or oblate circular internal section, with a smaller diameter region adapted to engage and grip the needle tip device, whereby a compressive load applied generally along the axis of larger diameter causes release of an unscrewed needle tip device from said grip ring. In another arrangement said grip ring is generally circular but resiliently compressible into engagement with said needle tip assembly.

Whilst the invention has been defined above, it extends to any inventive combination of the features set out above, or in the following description.

The invention may be performed in various ways, and an embodiment thereof will now be described by way of example only, reference being made to the accompanying drawings in which.

Figures 1, 2:
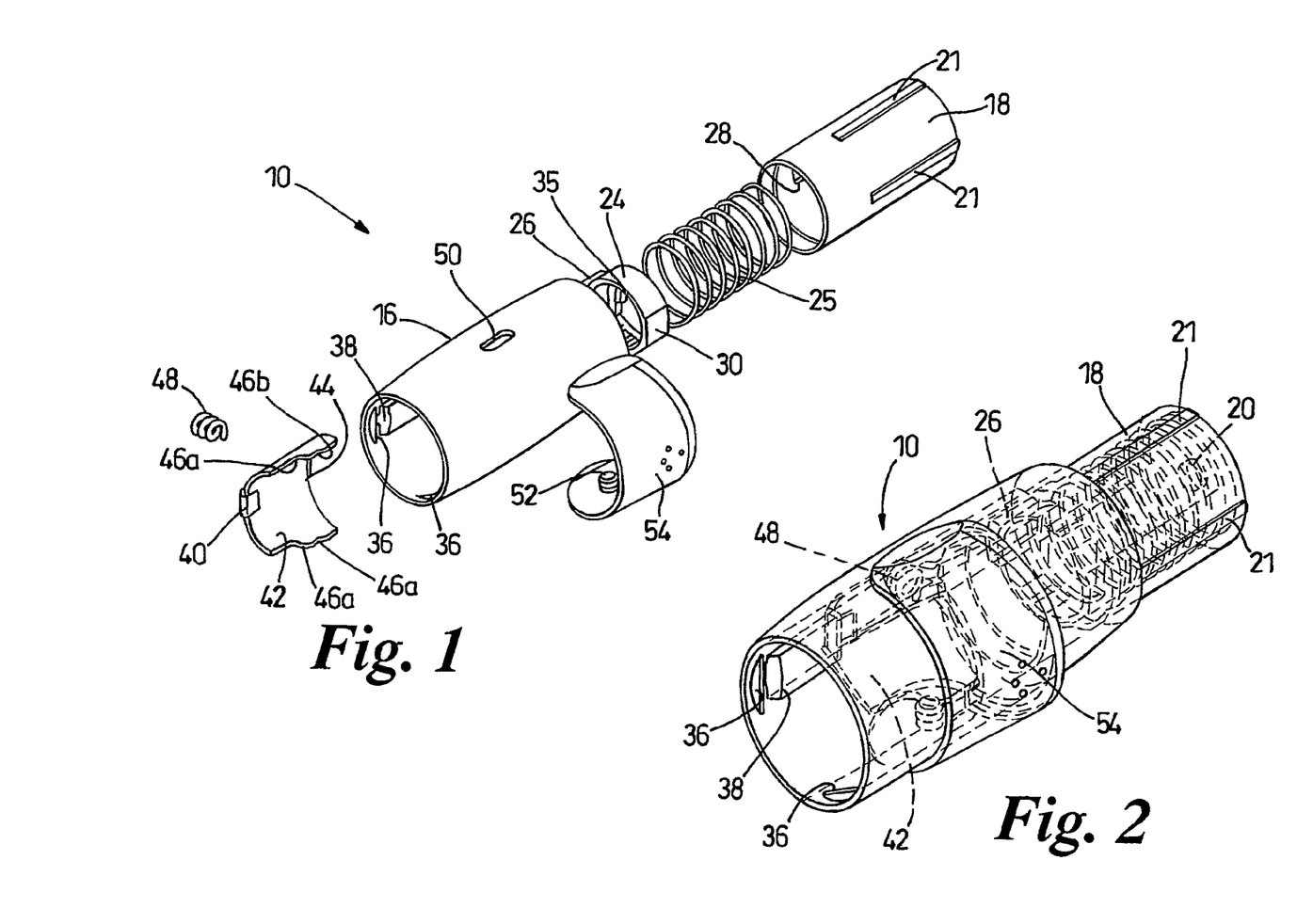
FIG. 1 is an exploded view of a needle shroud assembly in accordance with this invention.
FIG. 2 is a perspective view of the needle shroud assembly of FIG. 1 when assembled.
Figure 3:
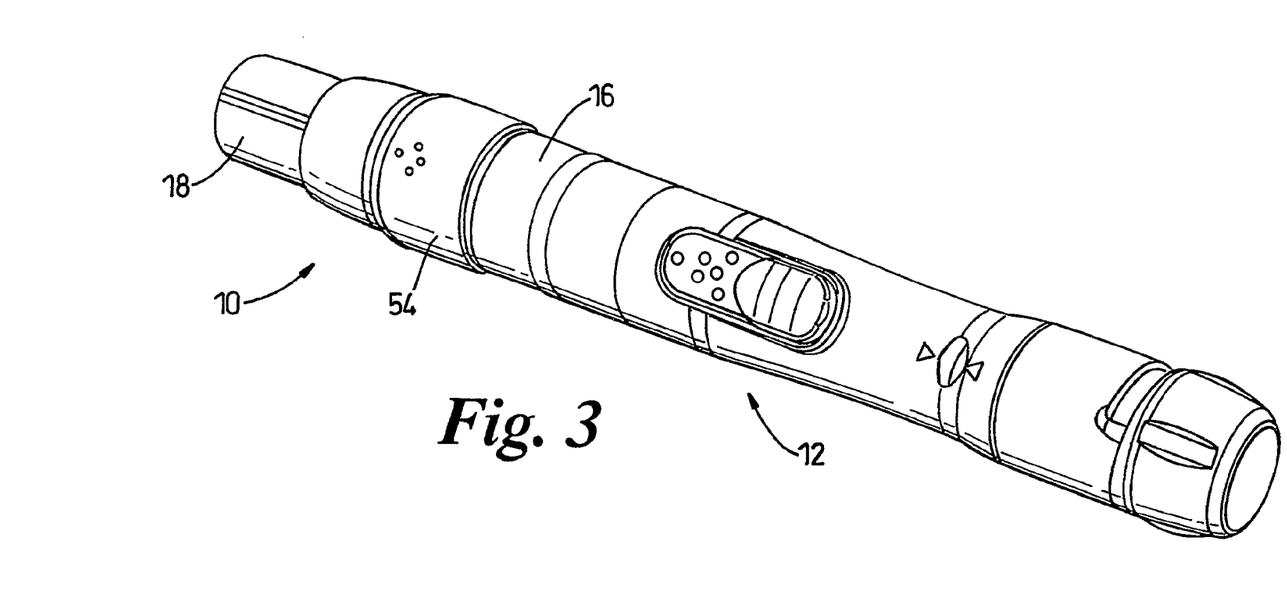
FIG. 3 is a general perspective view of the needle shroud assembly of FIGS. 1 and 2 when fitted to a pen-type injection device.
Figure 4:
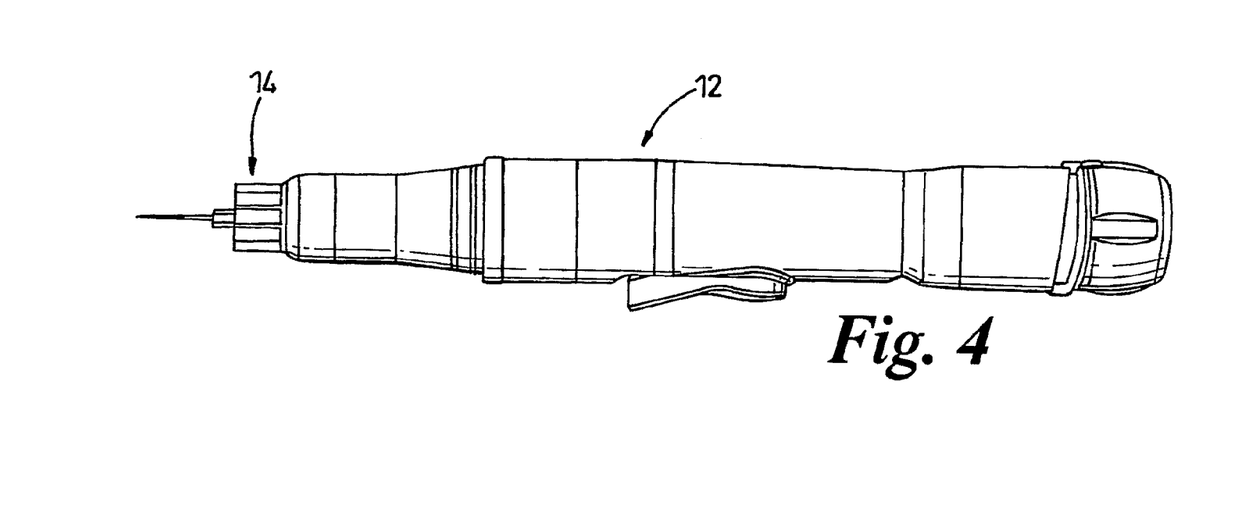
FIG. 4 is a view of the injection device with the needle shroud assembly removed and showing the needle tip device.

The needle shroud assembly 10 illustrated in the Figures is intended to be clipped or screwed onto the end of a pen-type injection device 12 containing a syringe and driver device (not shown) there being a needle tip device 14 screwed onto the end of the syringe (see FIG. 4). The injection device has a trigger and dosage selector and operates to deliver the required dose from the syringe.

Turning now specifically to FIGS. 1, 2 and 5 to 8, the needle shroud assembly comprises a barrel of moulded plastics material 16 which telescopically receives a needle shroud 18 of generally cylindrical form open at one end and closed at the other save for a needle hole 20. The needle shroud 18 has three equi-spaced longitudinal flutes 21 spaced at 90° on its outer surface which cooperate with corresponding radially inwardly directed fingers (not shown) on the barrel to keep the shroud 18 captive and non-rotatable. Instead of fingers and flutes being used to captivate the needle shroud, a stepped-in diameter may be used as a captivation means.

A grip ring 24 is slidably mounted within the needle shroud 18 and has an operating button 26 which protrudes through a slot 28 provided in the wall of the needle shroud 18. A compression spring 25 acts between the grip ring 24 and the needle shroud 18. The grip ring 24 engages the needle tip assembly 14 and so is axially restrained. Diametrically opposed to the button 26 on the grip ring 24 is a stepped region 30 which runs in a corresponding groove 32 in the needle shroud 18. In this particular embodiment the grip ring 24 is of non-circular ovoid or oblate internal section and is provided with splines 34 over its two smaller diameter arcs which are disposed at 90° to the operating button 26 (see FIGS. 9(a) and (b)). The splines cooperate with a corresponding section on the needle tip device 14 to render the two axially engagable but non-rotatable. The extent of movement of the grip ring 24 axially relative to the needle shroud is determined by the extent of the slot 28 and the groove 32 respectively, and the extent of axial movement of the grip ring relative to the needle tip device is limited by two chamfered lips 35.

The barrel 10 is provided with three equi-spaced ribs 36 which cooperate with an engagement portion on the injection device 12 to secure the needle shroud assembly to the injection device. Running forwardly from one of the ribs 36 is an axially directed abutment 38 the forward end of which is cupped to receive a hinge pin 40 which is integrally formed on the rear of arcuate saddle-shaped locking element 42. The locking element 42 has a forward arcuate abutment face 44 for cooperating with the rearwardly directed edge of the needle shroud 18. The locking element 42 is also provided with cam surfaces 46 which comprise rising portions 46(a) and detent portions 46(b). A compression spring 48 acts between the inner wall of the barrel 16 and a forward part of the locking element 42 to urge the forward part towards the centre of the barrel as seen more particularly in FIGS. 5 to 9.

The barrel 16 has two slots 50 through which project inwardly two spigots 52 integrally formed on an arcuate saddle-shaped actuating member 54. The spigots 52 project radially inwardly above the wall of the barrel 16 and act as cam elements to cooperate with the cam surfaces 46 and the locking element 42, again as seen in FIGS. 5 to 8.

Figure 5A:
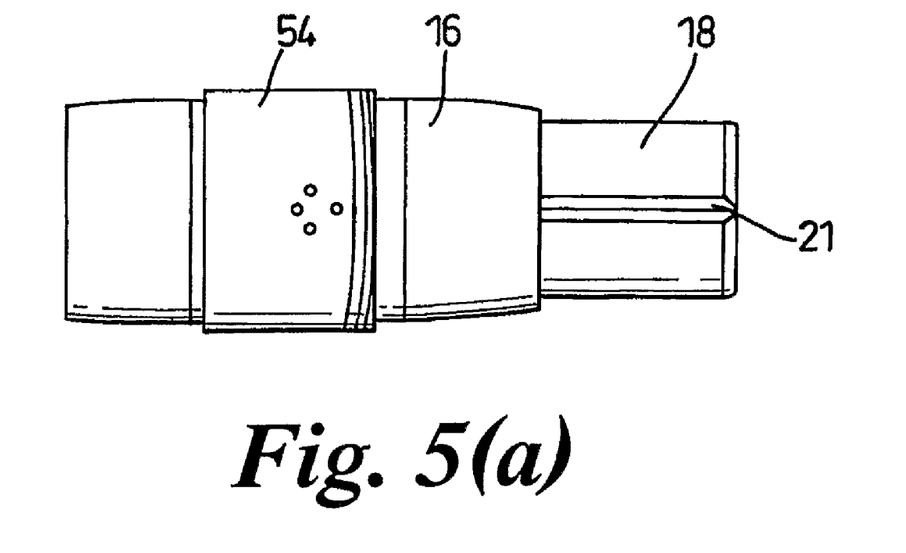
FIGS. 5(a) and (b) are respective side and section views showing the needle shroud assembly with the locking element in its safe position and the shroud fully extended.
Figure 5B:
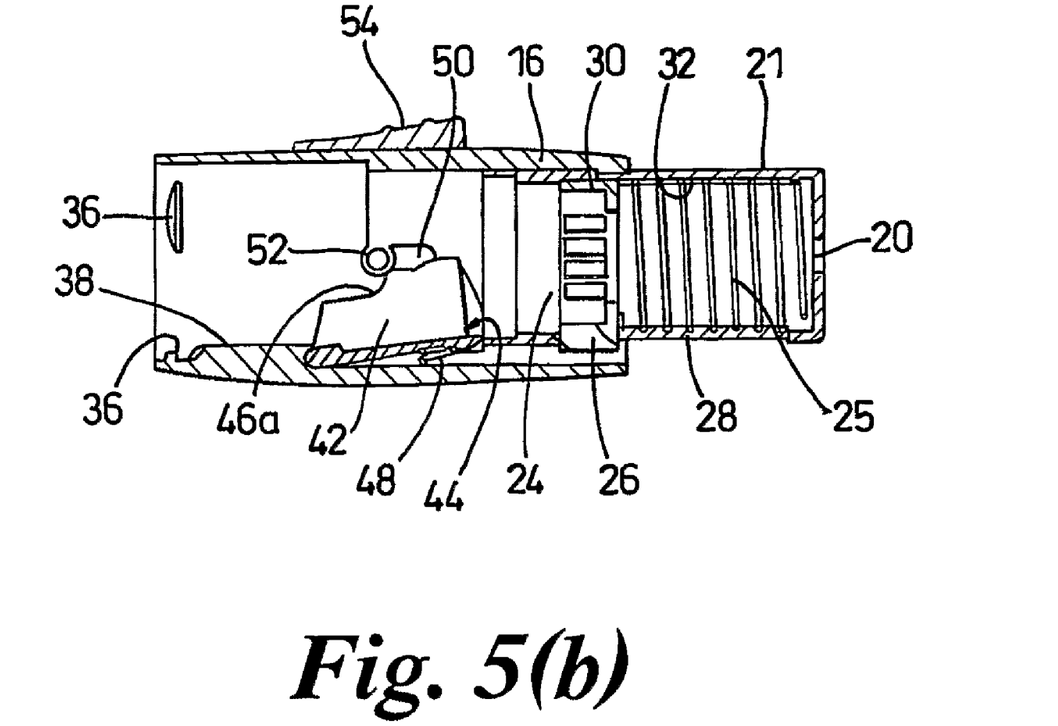

In operation, the needle shroud assembly at rest is in the position shown in FIGS. 5(a) and 5(b) with the needle shroud fully extended and the grip ring 24 at its rearmost position, urged to these positions by the compression spring 25 acting between them. In this position the forward edge of the locking element lies in the rearward path of the shroud and so cooperates therewith to limit or prevent rearward movement of the shroud.

Figure 6:
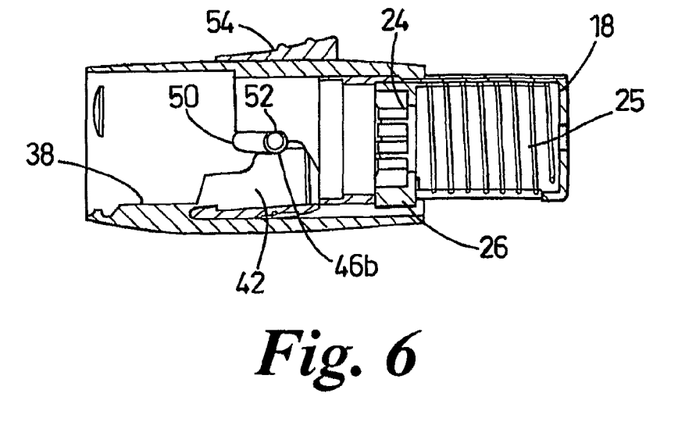
FIG. 6 is a section view showing the needle shroud assembly with the locking element in its live position and the shroud fully extended.

From this position, moving the actuating member 54 forwards drives the spigots 52 up and over the rising portions 46(a) of the cam surface 46 thus driving the locking element 42 away from the position in which it blocks rearward movement of the shroud 18, to a position flat against the inner wall of the shroud as shown in FIG. 6. At this position the spigots 52 are in the detent positions 46(b) of the cam surfaces.

Figure 7:
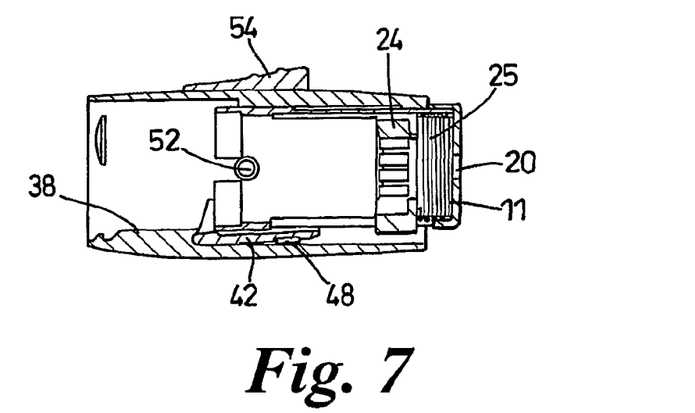
FIG. 7 is a section view showing the locking element riding on the side of the needle shroud at the point where the needle shroud is fully retracted and has returned the actuating member to its original position.
Figure 8:
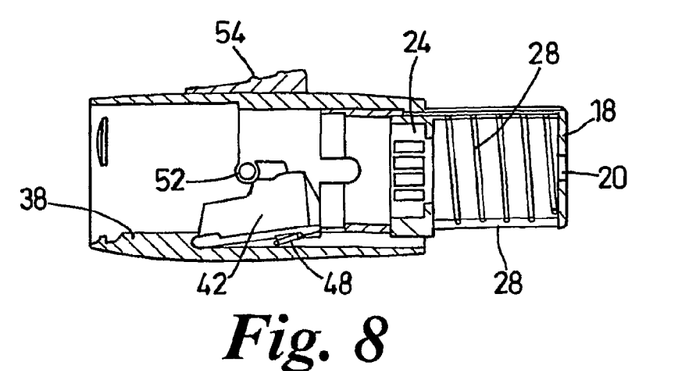
FIG. 8 is a section view showing the locking element in its safe position, the needle shroud fully retracted but the grip ring advanced relative to the needle shroud.

The shroud assembly can then be placed against the skin of the user and pushed so that the needle shroud 18 retracts, and the needle (not shown) penetrates the user's flesh. When the needle shroud approaches its fully retracted position, the spigots 52 are engaged by the proximal end wall of the needle shroud 18 to return the actuating member 54 to its original position as shown in FIG. 7. This means that the locking element 42 is no longer held flat against the wall, but is instead urged by the bias spring 48 against the outside of the needle shroud, but the compression spring 25 is sufficient to overcome this and to return the shroud 28 to the position shown in FIG. 8 with the locking element relatching to lock the shroud against retracting movement.

When it is required to remove the needle tip device, this can be done by rotating needle shroud assembly 10 relative to the rest of the injection device so that the grip ring 24 engages the corresponding surface on the needle tip device and unscrews it for the requisite number of turns, with longitudinal movement accompanying the unscrewing being accommodated by movement of the grip ring 24 against the compression spring 25.

Figure 9A:
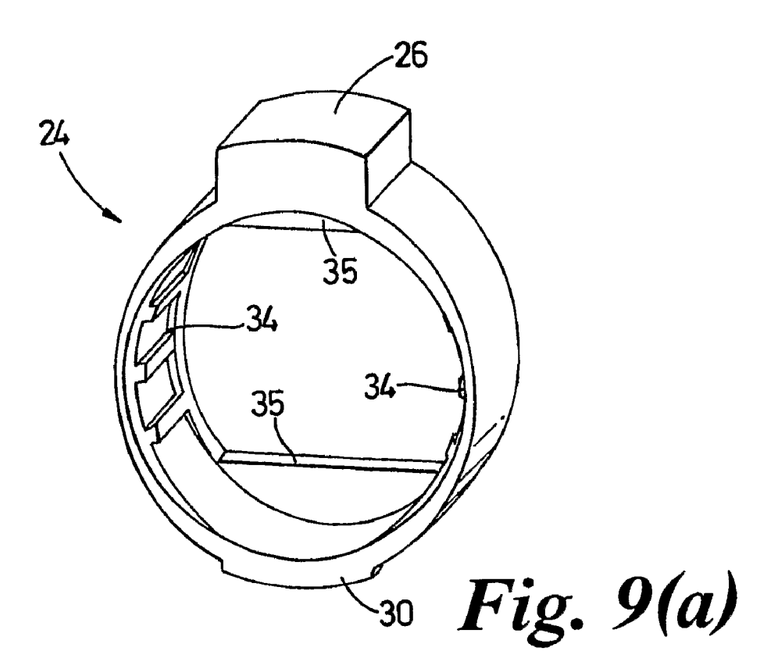
FIGS. 9(a) and (b) show the grip ring of the embodiment of FIG. 1 in the relaxed, ovoid shape, and the compressed circular shape respectively, and FIGS. 10(a) and (b) show an alternative form of grip ring in the relaxed and compressed states respectively.
Figure 9B:
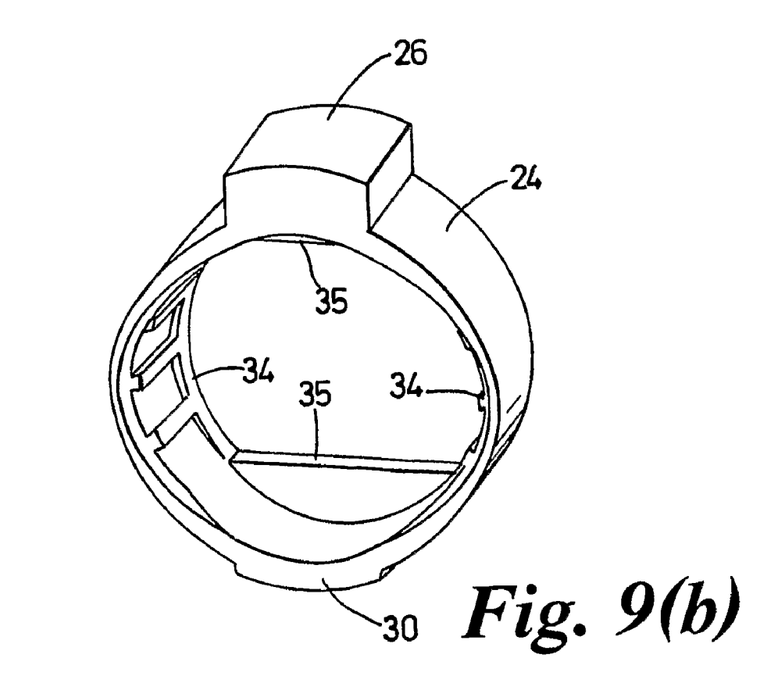

Having unscrewed the needle tip device 14, the needle shroud assembly 10 together with the gripped needle tip device, can be removed axially from the injection device, held over a sharps disposal bin and then button 26 pushed to move the grip ring from the position shown in FIG. 9(a) to that shown in FIG. 9(b), so that the used needle tip device drops out into the sharps bin.

Figure 10A:
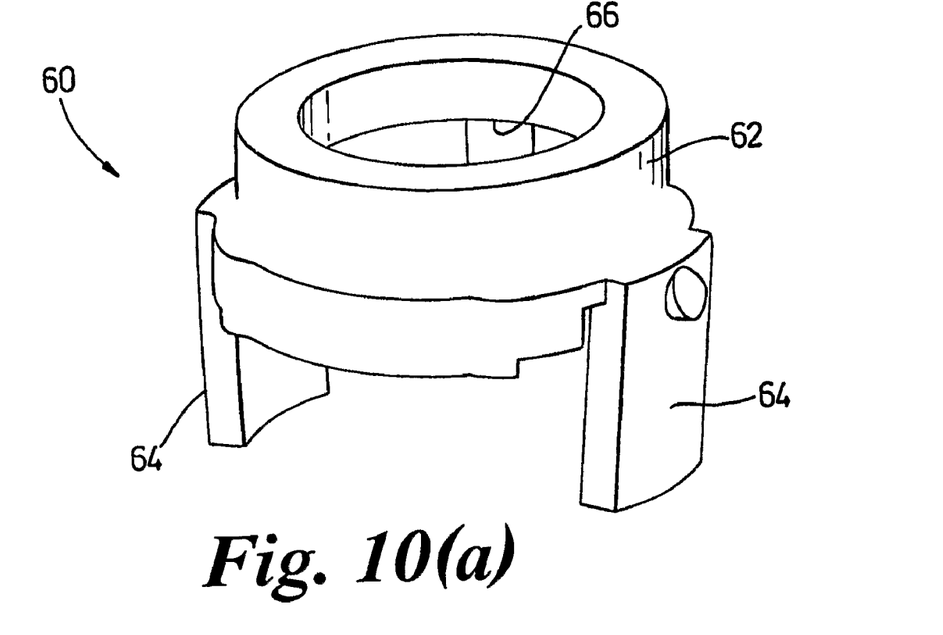
Figure 10B:
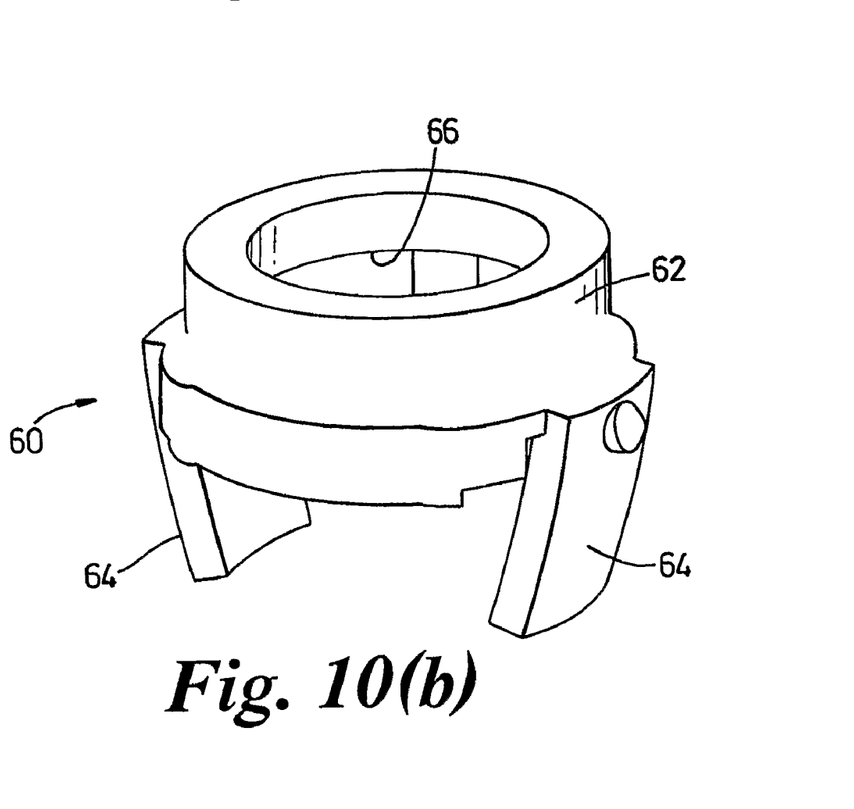

Referring now to FIGS. 10(a) and 10(b), there is shown an alternative form of grip ring 60, for being used in place of the grip 24. Here the grip ring comprises a relatively rigid collar portion 62 of circular form and two rearwardly extending, resiliently deformable, grip strip portions 64. In the relaxed state (FIG. 10(a)) the grip ring fits over a needle tip assembly 14 with radial clearance, but with the forward face of the splined collar of the assembly abutting an inner annular surface 66 of the collar portion which is biased into contact therewith by the spring 25. The inner circumference surface of the collar may be splined to engage the splines on the needle tip assembly. When it is wished to pull the unsecured needle assembly clear of the septum in the cartridge to which it is attached, one or both grip strip portions 64 are compressed to engage the side of the collar portion so that the needle tip can be pulled clear. Release of the grip strip portions allows the needle tip to be dropped into a sharps bin.

The invention claimed is:

1. A needle shroud assembly for a syringe holder for a syringe having a needle, comprising:
   a barrel,
   a needle shroud captively telescoped relative to the forward end of the barrel, for movement between a retracted position in which the needle of the syringe is exposed and an extended position in which the needle of the syringe is shrouded by the needle shroud,
   a shroud bias urging said shroud towards said extended position, said needle shroud normally being in said extended position under the urging of said shroud bias and being retractable from said extended position to said retracted position by a retraction movement applied against the urging of said shroud bias,
   a separate locking element mounted on one of said needle shroud and said barrel and movable,
   said locking element movable with respect to both said needle shroud and said barrel between i) a safe position in which said element prevents or limits the retraction movement of said needle shroud and ii) a live position in which the retraction movement of said needle shroud is not blocked thereby, and
   an externally operable actuating member movable to a release position to drive said locking element to said live position.

2. A needle shroud assembly according to claim 1, wherein said locking element is a saddle-shaped element of generally arcuate form.

3. A needle shroud assembly according to claim 1, wherein said locking element is pivotable between said safe and live positions.

4. A needle shroud assembly according to claim 1, wherein said locking element includes a bias part urging the locking element towards said safe position.

5. A needle shroud assembly according to claim 1, wherein said locking element is movably mounted on said barrel, and defines an extended arcuate abutment surface for cooperating with an associated region on said needle shroud.

6. A needle shroud assembly according to claim 1, wherein said locking element comprises at least one camming surface which cooperates with a corresponding cam element associated with or forming part of said actuating member, whereby longitudinal movement of said actuating member in the appropriate sense to a release position drives the locking element to said live position.

7. A needle shroud according to claim 6, wherein said camming surface includes a detent region whereby on moving said actuation member to said release position said actuation member is retained there by cooperation of the cam follower and the detent region.

8. A needle shroud assembly according to claim 1, where in use, as said needle shroud moves towards the retracted position, a surface thereon cooperates with said actuating member to move the actuating member back from the release position.

9. A needle shroud assembly according to claim 1, wherein said shroud bias comprises a compression spring acting between a distal region of the shroud and a grip ring which in use engages the needle tip device of the syringe.

10. A needle shroud assembly according to claim 9 adapted for use with a syringe onto which a needle tip assembly is screwed, wherein the grip ring is dimensioned in use non-rotatably to engage or be engageable with a flange or collar of the needle tip assembly, whereby said needle tip assembly may be unscrewed by rotating said needle shroud assembly in relation to said syringe.

11. A needle shroud assembly according to claim 10, wherein said grip ring is generally of ovoid or oblate circulate internal cross-section whereby in use a gripped needle tip assembly may be released by applying compression generally along the axis of greatest diameter of said section.

12. A needle shroud assembly according to claim 11, wherein said grip ring includes an operating button generally aligned with said axis of greatest diameter, said button being located in a longitudinal slot on said needle shroud to be externally accessible.

13. A needle shroud assembly according to claim 10, wherein said grip ring includes a resiliently compressible portion whereby in use a needle tip assembly may be gripped by applying compression to said grip ring.

14. A needle shroud assembly according to claim 9, wherein said grip ring has a castellated or splined inner cylindrical surface for cooperating with a correspondingly shaped surface on said needle tip device.

15. A needle shroud assembly for cooperating in use with a syringe having a needle tip device screwed thereon, comprising a needle shroud for shrouding said needle and slidably mounted with respect thereto a grip ring adapted in use non-rotatably to engage or be engageable with said needle tip device to allow unscrewing thereof, said grip ring being selected with regard to the needle tip assembly such that in a first configuration said grip ring grips said needle tip assembly non-rotatably and in a second configuration said grip ring fits with clearance around said needle tip assembly to allow release thereof, wherein one of said first and second configurations is a resiliently compressed state and the other is a relaxed state.

16. A needle shroud assembly according to claim 15 wherein said grip ring is of ovoid or oblate circular internal section adapted to engage the needle tip device along the minor diameter axis, whereby a compression load applied generally along the axis of larger diameter causes release of an unscrewed said needle tip device from said grip ring.

17. A needle shroud assembly according to claim 15, wherein said grip ring is resiliently compressible into engagement with said needle tip assembly.

18. A needle shroud assembly according to claim 1, wherein the needle is covered both before and during use of the needle for injection.

19. A needle shroud assembly for a syringe holder for a syringe having a needle, comprising:

a barrel, a needle shroud captively telescoped relative to the forward end of the barrel, for movement between a retracted position in which the needle of the syringe is exposed and an extended position in which the needle of the syringe is shrouded by the needle shroud, a shroud bias urging said shroud towards said extended position, said needle shroud normally being in said extended position under the urging of said shroud bias and being retractable from said extended position to said retracted position by a retraction movement applied against the urging of said shroud bias, a separate locking element mounted on said barrel, said locking element movable with respect to both said needle shroud and said barrel between (i) a safe position in which said locking element prevents or limits the retraction movement of said needle shroud and (ii) a live position in which the retraction movement of said needle shroud is not blocked thereby, a locking element bias biasing said locking element towards the safe position, and an externally operable actuating member movable to a release position to drive said locking element to said live position wherein, in use, as said needle shroud moves towards the retracted position, a surface thereon cooperates with said actuating member to move the actuating member back from the release position.

* * * * *